United States Patent [19]

Buder et al.

[11] Patent Number: 5,091,555

[45] Date of Patent: Feb. 25, 1992

[54] PROCESS FOR THE VACUUM DISTILLATION OF CRUDE CYANOHYDRINS CONTAINING 3 TO 6 CARBON ATOMS USING LIQUID JET PUMP

[75] Inventors: Wolfgang Buder, New Delhi, India; Udo Rudolph, Hanau, Fed. Rep. of Germany

[73] Assignee: Degussa AG, Fed. Rep. of Germany

[21] Appl. No.: 592,485

[22] Filed: Oct. 5, 1990

[30] Foreign Application Priority Data

Oct. 5, 1989 [DE] Fed. Rep. of Germany ....... 3933207

[51] Int. Cl.⁵ ................ C07C 253/30; C07C 253/34; C07C 253/00
[52] U.S. Cl. ...................................... 558/351; 558/451
[58] Field of Search ............................... 558/351, 451

[56] References Cited

U.S. PATENT DOCUMENTS

| | | | |
|---|---|---|---|
| 1,984,415 | 12/1934 | Macallum | 558/351 |
| 2,090,942 | 8/1937 | Fick | 558/351 |
| 2,101,823 | 12/1937 | Dittmar | 558/351 |
| 2,175,805 | 12/1937 | Jacobson | 558/351 X |
| 2,537,814 | 1/1951 | Davis | 558/351 |
| 2,745,865 | 5/1956 | Journeay | 558/351 |
| 2,826,601 | 3/1958 | Barsky | 558/351 |
| 4,745,207 | 5/1988 | Brunnmueller et al. | 558/351 |

FOREIGN PATENT DOCUMENTS

| | | | |
|---|---|---|---|
| 0273058 | 11/1989 | German Democratic Rep. | 558/351 |
| 0524797 | 2/1979 | U.S.S.R. | 558/351 |

*Primary Examiner*—Joseph Paul Brust
*Attorney, Agent, or Firm*—Cushman, Darby & Cushman

[57] ABSTRACT

A process for the purification of crude cyanohydrins which contain 3 to 6 carbon atoms, especially of crude acetone cyanohydrin, by distilling off the unreacted reactants namely hydrogen cyanide and the carbonyl compound. The purification becomes very simple, and the unreacted reactants can be fed directly into the cyanohydrin synthesis, when the vacuum is generated with a liquid jet pump. The exhaust vapors arising in the distillation or desorption are led into the driving jet of the pump, the liquid jet pump is driven with crude cyanohydrin which contains basic catalyst, and the exhaust vapors absorbed in the crude cyanohydrin are reacted to completion in a cooled reaction circuit in which the liquid jet pump is incorporated.

6 Claims, 2 Drawing Sheets

PROCESS FOR THE VACUUM DISTILLATION OF CRUDE CYANOHYDRINS CONTAINING 3 TO 6 CARBON ATOMS USING LIQUID JET PUMP

The present invention relates to a process for the purification of crude cyanohydrins containing 3 to 6 carbon atoms. The crude cyanohydrins are derived from hydrogen cyanide and the corresponding low-boiling carbonyl compound and contain those reactants as impurities. The unreacted reactants are separated from the crude cyanohydrins by distillation under vacuum and are re-cycled into the process of forming cyanohydrins. The process is particularly concerned with the purification of acetone cyanohydrin.

BACKGROUND OF THE INVENTION

A known method for the production of cyanohydrins is the base-catalyzed addition of hydrogen cyanide to carbonyl compounds, such as aldehydes and ketones. Cyanohydrins containing 3 to 6 carbon atoms are valuable intermediates. Acetone cyanohydrin is particularly important because it can be converted to methacrylate esters, and also to dimethylhydantoin derivatives and azobis(isobutyronitrile).

For the production of end products from cyanohydrins, the latter must often be available in very pure form, in general above 97%. Important impurities in crude cyanohydrins are unreacted reactants, that is hydrogen cyanide and low-boiling carbonyl compound, since the formation and dissociation of cyanohydrins set up an equilibrium. While cyanohydrin formation is base-catalyzed, the crude cyanohydrins are stabilized before work-up or purification by addition of an acid.

It is known to produce acetone cyanohydrin by continuously feeding the reactants acetone and hydrogen cyanide into alkaline catalyzed reaction circuits or into reactors formed as flow tubes. An equilibrium is established between the starting materials and acetone cyanohydrin at the reaction temperature—generally in the range 0°-50° C. In order to achieve high conversion in a practicable time, the reaction is usually carried out in several stages at decreasing temperature. The catalyst is then neutralized and, if necessary, separated, and the crude acetone cyanohydrin stabilized by making it weakly acidic. This permits the unconsumed starting materials to be separated under vacuum at temperatures up to 80° C. As far as possible, the reactants which are distilled off are re-circulated to the cyanohydrin reactor—cf. Ullmann's Encyclopedia of Industrial Chemistry, 5th ed. (1985) pages 91-92.

In the previously known processes, conventional apparatus, such as liquid ring pumps, vapor pumps or Roots blowers are used to provide a vacuum during the purification of the crude cyanohydrin. These systems, however, have significant disadvantages: in order to generate the vacuum required, multistage systems are necessary. These are more expensive and often require repairs. Such systems must further be followed by complicated installations for waste water treatment and/or waste gas washing. In addition, it was necessary to have intermediate condensation of the unconsumed reactants before their return to the cyanohydrin reactor.

SUMMARY OF THE INVENTION

The object of the present invention is to simplify the separation of the unreacted reactants of the cyanohydrin synthesis from hydrogen cyanide and a carbonyl compound—aldehydes and ketones containing 2 to 5 carbon atoms—and also to provide a method for purifying the cyanohydrin. A further object of the invention is to carry out this purification with a low cost system which requires a minimum of repair, which provides a substantially quantitative recycle of the reactants and which is easy to incorporate into the reaction circuit.

These and other objects are achieved in a process for the purification of crude cyanohydrins containing 3 to 6 carbon atoms, which contain unconsumed hydrogen cyanide and carbonyl compound by distilling off the unreacted reactants under vacuum and recovering the cyanohydrin from the separated reactants. In the process of the invention, the vacuum is generated with a liquid jet pump, the exhaust vapors arising during the distillation, which contain cyanohydrin reactants, are led without condensation or after only partial condensation, into the driving jet of the pump, the liquid jet pump is driven with crude cyanohydrin containing basic catalyst, and the liquid jet pump is integrated into a cooled reaction circuit in which the cyanohydrin reactants absorbed from the exhaust vapors react to completion to the cyanohydrin.

Preferably, the cyanohydrin is crude acetone cyanohydrin, the crude acetone cyanohydrin has a concentration exceeding 90% by weight and contains 1-5% by weight of hydrogen cyanide and 1-7% by weight of acetone, the unreacted reactants are distilled off from the crude acetone cyanohydrin at 40°-90° C. and a pressure of 35-100 mbar, the temperature in the cooled reaction circuit is kept at −10° C. to +10° C., and acetone is added, as required, to said cooled reaction circuit in an amount such that the reactants are present in approximately stoichiometric ratio.

It was not foreseeable that the above-mentioned problems could be simply solved by the use of a liquid jet pump driven by crude cyanohydrin, which is integrated into a simple reaction circuit consisting essentially of the liquid jet pump, a reactor and a pump and possibly a heat exchanger. Through the use of a liquid jet pump it is now possible, without the use of additional vacuum pumps and/or condensers, to generate the necessary vacuum, generally in the range of 30-100 mbar, and to absorb the reactants distilled off from the crude cyanohydrin directly into a reaction circuit and to allow them to react to completion to cyanohydrin.

The liquid jet pump is a type of pump which is well known. See for example Ullmann's Handbook of techn. Chemie, 3d Ed. 1951, Volume 1, page 47. As shown in FIG. 2, liquid is propelled under pressure from a nozzle 21 into an enlarged diameter pipe 22, causing a low pressure to form. Vapors are drawn through the entry zone 23 and mixed with the liquid as it flows through the pipe 2.

The liquid jet pump can be equipped with a conventional nozzle. In order to avoid cavitation in the nozzle in the absence of inert gases and/or to increase the gas-liquid exchange surface, the nozzle can also be multiply slotted—for liquid jet pumps with such or similarly-formed nozzles the term liquid jet condensers is also conventional.

The process according to the invention can be used for the purification of crude cyanohydrins containing 3 to 6 carbon atoms, preferably for the purification of crude cyanohydrins with a concentration of more than 90% by weight in addition to 1-5% by weight of hydrogen cyanide and 1-7% by weight of un-reacted carbonyl compound. The process is especially suitable for the purification of crude lactonitrile, 2-hydroxy-n-butyronitrile, acetone and methyl ethyl ketone cyanohydrin; more especially preferred is the purification of crude acetone cyanohydrin.

The exhaust vapors arising from the distillation of the crude cyanohydrin in general contain, apart from hydrogen cyanide and the carbonyl compound, some water and some cyanohydrin. The ratio of hydrogen cyanide to carbonyl compound in the exhaust vapors depends both on the pressure and temperature conditions of the evaporator used and on the stoichiometric ratio of the reactants during the cyanohydrin synthesis. In the case of higher-boiling carbonyl compounds and/or an excess of HCN, the exhaust vapors will contain a correspondingly high concentration of HCN.

According to the invention, the liquid jet pump is driven with crude cyanohydrin which contains a sufficient amount of basic catalyst or is circulated over a basic fixed bed catalyst, so that the exhaust vapor constituents absorbed in the crude cyanohydrin are converted to the corresponding cyanohydrin. To the reaction circuit in which the liquid jet pump is incorporated are added catalysts which are known per se, e.g., alkali hydroxides, alkali carbonates, amines or anion exchangers. As necessary, additional carbonyl compound can be fed to the reaction circuit in order to adjust the desired molar ratio of the reactants. This may be necessary in particular when the exhaust vapors contain too little carbonyl compound.

The reaction circuit mentioned can be integrated into the cyanohydrin production process or connected downstream of this. The reaction temperature is maintained between −10° C. and +30° C., preferably between −10° C. and +10° C. Since the cyanohydrin formation proceeds exothermically, since the equilibrium between the reactants and the cyanohydrin is displaced at low temperatures in favor of the cyanohydrin, and since the absorption of the exhaust vapors is also favored at low temperature and leads to a lower vapor pressure of the system, the reaction mixture present in the reaction circuit is preferably cooled before it enters the liquid jet pump.

From the reaction mixture, called "crude cyanohydrin", obtained after a single or multistage reaction, preferably at decreasing temperature, followed by neutralization of the catalyst and acid stabilization, the unreacted reactants are distilled off, under which is also understood a desorption. In principle, evaporators of different designs can be used for this distillation or desorption. On account of the thermal instability of the cyanohydrins, it is preferred to use systems which impose only moderate and especially brief thermal stress; thin-film evaporators, such as falling-film evaporators, are preferred. The separation of the reactants from the crude cyanohydrin occurs preferably in the range of 30°–90° C. at a pressure of 35–100 mbar. A temperature above 90° C. is generally less recommended; at a temperature around or below 30° C., the carbonyl compound, with the possible exception of acetaldehyde, can no longer satisfactorily be distilled off or desorbed from the reaction mixture. For the purification of crude acetone cyanohydrin the evaporator is preferably operated at 40°–90° C. and a pressure of 35–100 mbar, especially 40–60 mbar. The exhaust vapors of the evaporator can be absorbed directly by the crude cyanohydrin by means of the liquid jet pump; if desired, for partial condensation of the exhaust vapors to relieve the liquid jet pump, a simple condenser can be interposed, the condensate also being fed into the reaction circuit.

DETAILED DESCRIPTION OF PREFERRED EMBODIMENT

Figure 1:
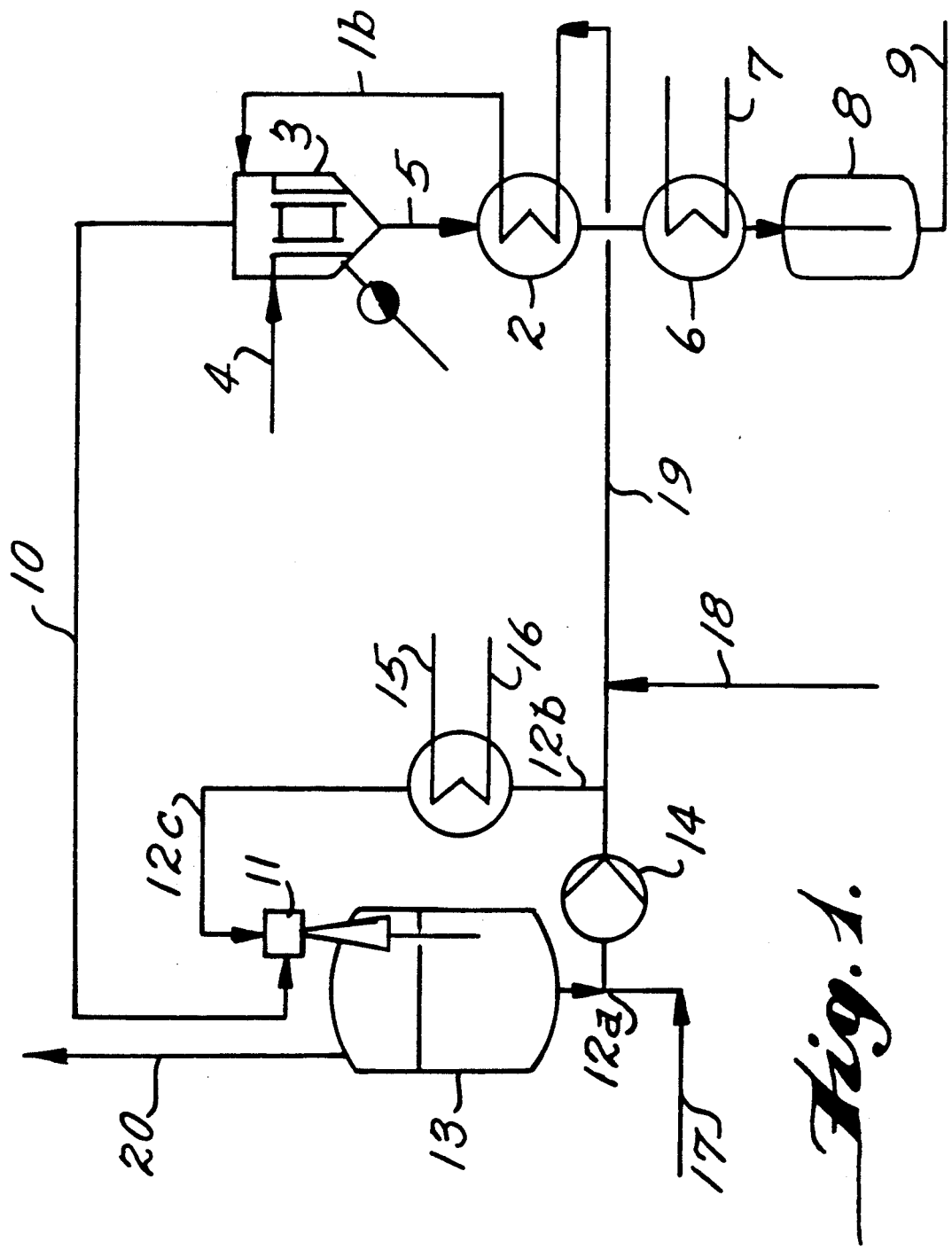
Figure 2:
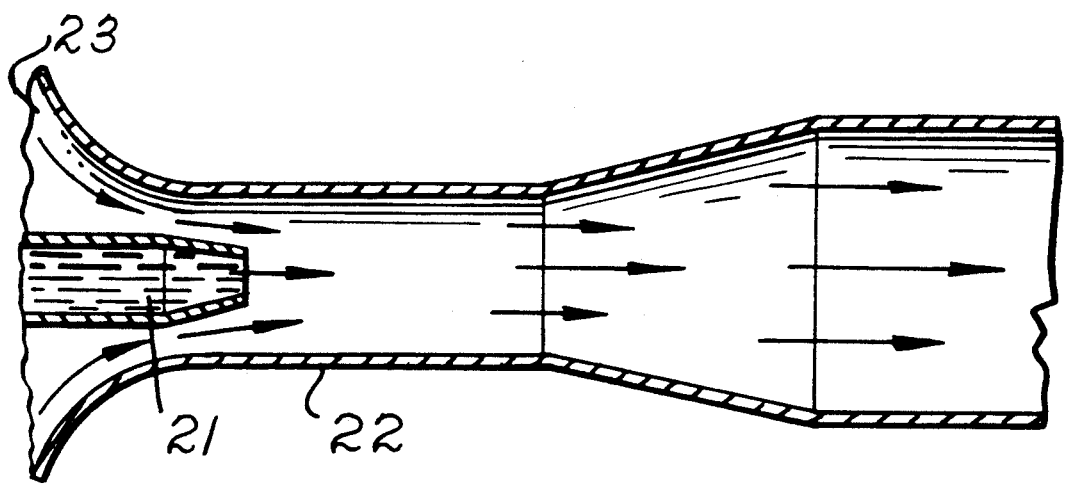

A preferred embodiment of the process, on which the example also is based, can be better understood from the following description, reference being made to the FIG. 1 which illustrates a reaction circuit in schematic form.

The crude cyanohydrin in stabilized form—usually adjusted with $H_2SO_4$ to pH 1–3—is fed through line (1a), and pure cyanohydrin is removed through line (9). After passage through a heat exchanger (2), the heated crude cyanohydrin is fed via line (1b) to the evaporator (3), which is heated via (4). The exhaust vapors pass via line (10) to the liquid jet pump (11), and the purified cyanohydrin via line (5) and the heat exchangers (2) and (6) being cooled via (7) with cooling water, to the tank (8). The exhaust vapors (10) are sucked off by the liquid jet pump (11), dissolve spontaneously in the operating liquid and react in the reaction circuit to cyanohydrin. The reaction circuit, in which the liquid jet pump (11) is incorporated and in which there is catalyst-containing crude cyanohydrin, further includes the reactor (13), the pump (14), the heat exchanger (15) and the recycle line (12a), (12b) and (12c). The pump (14) provides for the necessary recycle and pressure of the operating fluid before the liquid jet pump (11); the heat exchanger (15), supplied with cooling water or cooling brine through line (16), provides for the cooling of the operating liquid. The carbonyl compound and basic catalyst can be fed to the system through line (17). In order to keep the level constant in the reactor (13), freshly formed cyanohydrin is drawn off continuously via line (19), neutralized and stabilized by addition of an acid via line (18) and added to the stabilized crude cyanohydrin flowing through line (1a). Line (20) signifies the waste gas line through which inert gases with in essence a very small content of hydrogen cyanide—corresponding to the partial pressure over the liquid in the reactor (13)—are led out of the system and to a waste gas wash, for detoxification or combustion. If the carbonyl compound is fed through line (17), it preferably is first used as a washing medium in a waste gas wash for the hydrogen cyanide removed via line 20. The kinetics of the cyanohydrin formation at the temperature prevailing in the reactor (13) determines the required residence time and with that the volume of the reactor.

The process according to the invention is, as has been shown, simple to manipulate and can be operated safely using simple apparatus. According to the invention the cyanohydrin content of 90–95% by weight can be raised without any difficulty to above 97% by weight.

EXAMPLE

The following example is directed to the purification of crude acetone cyanohydrin (=crude ACH) in a pilot plant according to the drawing. The operating conditions are as follows:

| | |
|---|---|
| Temperature of the crude ACH fed to the evaporator (3) | 40° C. |
| Temperature of the pure ACH leaving the evaporator (3) | 85° C. |
| Distillation pressure in the evaporator (3) | 50 mbar |
| Temperature of the reaction mixture in the reactor (13) | 0° C. |

-continued

| | |
|---|---|
| Temperature of the reaction mixture in the line (12c) before the liquid jet pump (11) | −3 C. |
| Pressure of the reaction mixture in the line (12c) before the liquid jet pump (11) | 5 bar |
| Amount of crude ACH fed through line (1a/1b) into the evaporator (3) | ca. 1500 kg/h 94% by wt. |
| Amount of pure ACH withdrawn through line (9) | ca. 1500 kg/h 98.5% by wt. |
| Amount of crude ACH drawn off from reactor (13) and recycled via line (19) to the evaporator | ca. 140 kg/h 90% by wt. |
| Amount of acetone metered in via line (17) to the reaction circuit | ca. 25 kg/h |
| Amount of exhaust vapors | ca. 115 kg/h |
| Composition of the exhaust vapors in line (10) | 43% ACH 25% HCN 37% acetone |
| Amount of absorption/reaction recycle stream circulated by pump (14) | ca. 20 m³/h |

What is claimed is:

1. In a process for the purification of a crude cyanohydrin, said cyanohydrin being selected from the group consisting of lactonitrile, 2-hydroxy-n-butyronitrile, acetone cyanohydrin and methyl ethyl ketone cyanohydrin, said crude cyanohydrin containing unreacted hydrogen cyanide and the carbonyl compound from which the cyanohydrin has been made, said process comprising distilling off the unreacted reactants under vacuum at a temperature between 30° and 90° C. and a pressure of 35–100 mbar and recovering the cyanohydrin from the separated reactants;

the improvement in which the vacuum for the distillation is generated with a liquid jet pump, the exhaust vapors arising during the distillation, which contain unconsumed cyanohydrin reactants, are led without condensation or after partial condensation into the driving jet of the pump, whereby the driving jet in the liquid jet pump consists of crude cyanohydrin containing basic catalyst and the liquid jet pump is integrated into a cooled reaction circuit in which the cyanohydrin reactants, absorbed from the exhaust vapors, react to completion to the cyanohydrin.

2. A process according to claim 1 in which the crude cyanohydrin is crude acetone cyanohydrin.

3. A process as set forth in claim 2 in which the crude acetone cyanohydrin has a concentration exceeding 90% by weight and contains 1–5% by weight of hydrogen cyanide and 1–7% by weight of acetone.

4. A process as set forth in claim 2 in which the unreacted reactants are distilled off from the crude acetone cyanohydrin at 40°–90° C. and a pressure of 35–100 mbar.

5. A process as set forth in claim 2 or claim 4 in which the temperature in the reaction circuit is kept at −10° C. to +10° C.

6. A process as set forth in claim 2 or claim 4 in which, as required, acetone is added to said cooled reaction circuit in an amount such that the reactants are present in approximately stoichiometric ratio.

* * * * *